United States Patent [19]

Auchincloss

[11] Patent Number: 4,777,018

[45] Date of Patent: Oct. 11, 1988

[54] METHOD OF DISINFECTING PREMISES FROM COCCIDIAL OOCYSTS USING GENERATED AMMONIA

[76] Inventor: Thomas R. Auchincloss, The Grange, Stanningfield, Bury St., Edmunds, Suffolk 1P14 4RD, United Kingdom

[21] Appl. No.: 14,763

[22] PCT Filed: Jun. 2, 1986

[86] PCT No.: PCT/GB86/00307

§ 371 Date: Mar. 23, 1987

§ 102(e) Date: Mar. 23, 1987

[87] PCT Pub. No.: WO86/06934

PCT Pub. Date: Dec. 4, 1986

[30] Foreign Application Priority Data

Jun. 1, 1985 [GB] United Kingdom ............... 8513849
Oct. 11, 1985 [GB] United Kingdom ............... 8525180

[51] Int. Cl.$^4$ ................... A61L 2/18; A61L 2/20; A01N 25/02; A01N 59/00
[52] U.S. Cl. ....................................... 422/28; 422/29; 422/32
[58] Field of Search ................ 422/3, 28, 29, 32, 37; 424/166, 405

[56] References Cited

U.S. PATENT DOCUMENTS 4,084,747 4/1978 Alliger .......................... 422/37 X

FOREIGN PATENT DOCUMENTS 1362963 8/1974 United Kingdom .

*Primary Examiner*—Barry S. Richman
*Assistant Examiner*—Timothy M. McMahon
*Attorney, Agent, or Firm*—Collard, Roe & Galgano

[57] ABSTRACT

A method of disinfecting premises from coccidial oocysts in which surface to be disinfected is thoroughly wetted with a first aqueous solution of ammonium salt containing approximately 0.5 to 1.5 molar of ammonium together with non-ionic surfactant and indicator having a color change in the region of pH 8 to pH 10 and the wetted surface is then covered with sufficient of a second aqueous solution of alkali metal hydroxide containing approximately 0.75 to 2.3 molar of hydroxide toether with phenolic bactericide to cause the indicator to change color on the treated surface. A preparation for use in such a method comprises a first package containing ammonium salt together with non-ionic surfactant and indicator and second package containing alkali metal hydroxide and phenolic bactericide, the molar amount of hydroxide in the second package being greater than the molar amount of ammonium in the first package.

3 Claims, No Drawings

METHOD OF DISINFECTING PREMISES FROM COCCIDIAL OOCYSTS USING GENERATED AMMONIA

This invention relates to a method of disinfecting premises from coccidial oocysts. Coccidiosis is a disease affecting livestock particularly poultry especially in a warm humid environment. The disease is caused by certain protozoa referred to generally as coccidia of which various species of Eimeria have been identified and shown to be pathogenic to livestock. The disease is spread by oocysts of the coccidia which are resistant to a wide variety of normal disinfectant materials and in many instances can persist in the environment for a very long period of time. For example, oocysts of *Eimeria chandallis*, an important parasite of sheep, are highly resistant to the environment under normal conditions.

In intensive livestock husbandry the premises are generally cleaned and disinfected at the end of each cropping period before re-stocking with young livestock. Unless special precautions are taken, coccidial oocysts left in the environment, particularly on the floor and lower walls of the premises, quickly infect the new livestock to an extent beyond ready control by coccidiastatic medicaments which may be given in the feed.

The most effective chemical agent yet found to control coccidia is ammonia. However the use of aqueous ammonia or ammonia gas is objectionable, not least because of its effects on the operator.

In British patent specification No 1362963 it was proposed to disinfect premises both from coccidia and from bacteria by the use of three components which were added in sequence to water resulting in solubilization of the bactericide and interaction of the chemicals present to produce ammonia gas. In a typical example, sodium hydroxide pellets (728 g, 18.2 moles) were dissolved in water (18.2 liters), ammonium chloride (1110 g, 20.75 moles) was then stirred in and dissolved readily, and finally the bactericide 5,5'-dichloro-2,2'-dihydroxy diphenyl monosulphide (91 ml of 38-42% solution) was added to produce an aqueous disinfectant solution ready for spraying in poultry houses.

However, the procedure described had the drawback that too much gaseous ammonia was released into the atmosphere. This made it necessary for the operator to use a respirator and also depleted the concentration of ammonia at the surfaces where action on the oocysts was required. For good results the premises had to be sealed during and after application of the disinfectant solution.

According to the present invention, there is provided a method of disinfecting premises from coccidial oocysts in which surface to be disinfected is thoroughly wetted with a first aqueous solution of ammonium salt containing approximately 0.5 to 1.5 (preferably 0.8 to 1.0) molar of ammonium together with non-ionic surfactant and indicator having a colour change in the region pH 8 to pH 10 and the wetted surface is then covered with sufficient of a second aqueous solution of alkali metal hydroxide containing approximately 0.75 to 2.3 (preferably 1.2 to 1.5) molar of hydroxide together with phenolic bactericide to cause the indicator to change colour on the treated surfaces.

In the method of the invention, ammonia is liberated only at the surface where it is required, and the amount of ambient gaseous ammonia is very much less than in the earlier method. There is a better disinfecting effect against coccidial oocysts, and it is no longer necessary for the opeator to use a respirator.

The molar concentration of hydroxide in the second aqueous solution is preferably significantly greater than the molar concentration of ammonium in the first aqueous solution.

The fact that the ammonia is liberated in situ means that the method of the invention can be used effectively in open-sided livestock premises. The reaction liberating ammonia takes place in the infected sites with minimal loss of ammonia and maximum kill of the oocysts. The surfactant in the first aqueous solution ensures penetration of rough surfaces and cracks where oocysts are to be found. The indicator turns colour when the second aqueous solution comes in contact with surfaces wetted with the first aqueous solution and thus guides the operator in his application of the second aqueous solution.

The method of the invention is suitable for poultry, pig, calf and sheep housing, and has resulted in 99.9% reduction in oocysts and 99.9% reduction in bacterial population of infected sites.

The ammonium salt may be one or more of ammonium chloride, ammonium sulphate, and ammonium salts of other inorganic and organic acids.

The alkali metal hydroxide is for economic reasons preferably sodium hydroxide although the hydroxides of potassium and other alkali metals may be used.

The phenolic bactericide may be any such material suitable for killing bacteria in an aqueous alkaline medium. In particular, it may be chosen from the following compounds:

5,5'-dichloro-2,2'-dihydroxy diphenyl monosulphide;
5,5'-dichloro-2,3'-dihydroxy diphenyl methane;
p-chloro-m-cresol;
p-chloro-m-xylenol;
2,4-dichloro-3,5-dimethyl phenol;
o-phenyl phenol;
4-chloro-2-phenyl phenol;
trichlorophenol.

The indicator may be any water-soluble indicator showing a colour change in the range pH 8 to pH 10. Phenolphthalein is particularly suitable because it is colourless at lower pH and becomes intensely red at higher pH thus clearly demonstrating to the operator the areas which have been successfully covered according to the method of this invention. Other indicators which may be used include:

alpha-naphtholphthalein;
o-cresolphthalein;
p-naphtholbenzein;
quinizarin sulphonic acid;
thymol violet;
thymolphthalein;
alizarin yellow GG;
alizarin yellow.

The sulfactant is non-ionic and may for example be one or more of the following:

polyglycol ethers of fatty alcohols;
fatty acid ethylene oxide condensates;
polyglycol ethers of alkyl phenols;
ethylene oxide propylene oxide condensates;
nonyl phenol ethoxylates;
fatty alcohol ethoxylates;
lauryl ether sulphates.

Anionic surfactant may also be present, for example sodium dodecyl sulphonic acid.

According to the present invention there is also provided for use in the above-described method a preparation comprising two packages, the first package containing ammonium salt together with non-ionic surfactant and indicator and the second package containing an alkali metal hydroxide and phenolic bactericide, the molar amount of hydroxide in the second package being greater than the molar amount of ammonium in the first package preferably by a factor of at least 1.2 but not more than 2.0.

The first package carries instructions for the contents to be dissolved in water the amount of which will be sufficient to give an ammonium concentration of approximately 0.5 to 1.5 molar. This solution is then applied first to the surfaces to be treated.

The second package carries instructions to dissolve the contents in a similar amount of water to give a solution containing approximately 0.75 to 2.3 molar of hydroxide which is then applied as quickly as possible over the surfaces already treated with the solution of the contents of the first package.

The following examples illustrates the invention.

EXAMPLE 1

A mixture of the following solid ingredients ammonium chloride (1.4 kg), non-ionic surfactant principally polyglycol ethers of fatty alcohols (63 g) and phenolphthalein (1.2 g) was dissolved in 30 liters of water and applied to 100 square meters of surface to be disinfected.

A solid mixture of sodium hydroxide (1.6 kg) and 5,5'-dichloro-2,2'-dihydroxy diphenyl monosulphide (34 g) was dissolved in 30 liters of cold water and applied as soon as possible onto the same area. This ensured that ammonia was formed in the presence of sufficient water on the surfaces and particularly in the cracks and crevices where coccidial oocysts were to be found.

The amount of ammonia escaping into the atmosphere was relatively very small in comparison with previously known methods of applying ammonia for control of coccidial oocysts. There was no need for the operator to use a respirator.

The above-described procedure was used on a farm in Norfold England where broiler chickens were raised on earth floors and which had a long history of coccidial infection. Earth plug samples were taken randomly from the floor, six before and six after treatment, and counts were made of oocysts per gramme of soil. The results are given in the following table.

|    | Before Treatment | After Treatment |
|----|------------------|-----------------|
| 1. | 100              | 0               |
| 2. | 200              | 0               |
| 3. | 0                | 0               |
| 4. | 300              | 0               |
| 5. | 0                | 0               |
| 6. | 100              | 0               |

The above-described method was also used to disinfect premises on a farm where laying hens were reared on earth floor litter houses. All surfaces were thoroughly cleaned and the entire house and earth floor were power-washed with solutions according to the invention. The disinfected house was then used for the rearing of pullets, and after eighteen weeks the oocysts count was nil. There was also a nil count of ascaridia and capillaria eggs both of which had been present at the level of one hundred eggs per gramme in the untreated floor. The subsequent performance of the birds from the treated house reflected their freedom from internal parasites by better feed utilisation. The disinfection technique of the invention proved to be a valuable aid in lowering the incidence of parasites in the floor-reared pullets on this farm.

EXAMPLE 2

The efficacy of the invention was tested against *Eimeria chandallis*, an important parasite of sheep having highly resistant oocysts which cause disease especially when ewes are brought indoors for lambing.

A solid mixture of ammonium chloride (4.78 g), non-ionic surfactant principally polyglycol ethers of fatty alchols (215 mg) and phenolphthalein (4 mg) was dissolved in 50 ml of water.

A solid mixture of sodium hydroxide (4.90 g) and 5,5'-dichloro-2,2'-dihydroxy diphenyl monosulphide (104 mg) was dissolved in 50 ml of water.

The solutions were combined in the presence of a suspension of oocysts of *Eimeria chandallis* so that the resultant dilution v/v of the original combined solutions was 1/10, 1/100 or 1/500. The diluted solutions containing oocysts were then held at 4° C. or 20° C. and samples were taken after 1 hour, 6 hours and 24 hours to see whether the oocysts had been killed. The oocysts in each sample were washed using several changes of saline. They were then incubated overnight in a solution of sodium bicarbonate (1.4%) to which phenol red had been added, and carbon dioxide was bubbled through until the colour was lost. The oocysts were then washed with saline and resuspended in phosphate-buffered saline at pH 7.6. Glass balls were added and the suspensions were shaken until the shells of the oocysts ruptured releasing sporocytes. A sample was then removed and added to a solution of 0.25% trypsin in 0.5% w/v bile and incubated at 37° C. for up to 45 minutes or until excystment was seen to occur.

The results were as follows ("+"=excystment).

|              |          | Time when sample taken |         |          |
|--------------|----------|------------------------|---------|----------|
| Temperature  | Dilution | 1 hour                 | 6 hours | 24 hours |
| 4° C.        | 1/10     | −                      | −       | −        |
| 4° C.        | 1/100    | +                      | −       | −        |
| 4° C.        | 1/500    | +                      | +       | +        |
| 20° C.       | 1/10     | −                      | −       | −        |
| 20° C.       | 1/100    | +                      | −       | −        |
| 20° C.       | 1/500    | +                      | −       | −        |

These results show that the materials of the invention were effective against *Eimeria chandallis* at a dilution of 1/100 even at 4° C., and at 20° C. all oocysts were killed after one hour's exposure at a dilution of 1/100 or after six hours' exposure at a dilution as high as 1/500.

EXAMPLE 3

The efficacy of the invention was tested in preventing the excystment of sporulated avian oocysts.

The sporulated oocysts were obtained from the Parasitology Department of the Central Veterinary Laboratory, Weybridge. The strains of Eimeria used in the trial were:

*Eimeria tenella* W264
*Eimeria necatrix* W71
*Eimeria brunetti* W63
*Eimeria acervulina* W102

Each coccidial suspension was prepared separately in monoculture. Day-old chicks were housed in isolation until 3-4 weeks. During the rearing period faecal samples from the birds were examined twice weekly before oral inoculation with the test strain of oocyst. To prevent cross contamination each species of oocyst was handled in separate isolation facilities by staff having no contact with other birds.

At 5-8 days after inoculation, depending on the species of coccidia, faeces was collected, suspended in water and screened. Finally, the oocysts were harvested by flotation in concentrated sodium chloride solution. The harvested oocysts were then washed and re-suspended in 2% potassium dichromate solution. Sporulation of the oocysts was achieved by incubating the suspensions at 27° C. for 7 days. The final suspensions supplied by the Parasitology Department contained the following proportion of sporulated oocysts:

Eimeria tenella 95% sporulated
Eimeria necatrix 85% sporulated
Eimeria brunetti 83% sporulated
Eimeria acervulina 82% sporulated Before use of each suspension was washed with phosphate buffered saline (PBS) at a pH of 7.6 to remove the potassium dichromate solution. The washed suspensions were standardised to a concentration of 100,000 oocysts per milliliter in PBS.

A solid mixture of ammonium chloride (4.78 g), non-ionic surfactant principally polyglycol ethers of fatty alcohols (215 mg) and phenolphthalein (4 mg) was dissolved in 50ml of water.

A solid mixture of sodium hydroxide (4.90 g) and 5,5'-dichloro-2,2'-dihydroxy diphenyl monosulphide (104 mg) was dissolved in 50 ml of water.

The solutions were combined in the presence of each of a suspension of each avian oocyst so that the resultant dilution v/v of the original combined solutions was neat, 1/10, or 1/100: to test the neat solution of 9 ml of oocyst suspension was re-suspended in a combination of 10 ml of the original combined solutions.

To test the 1/10 solution, 1 ml of original combined solution was added to 9 ml of oocyst suspension.

The efficacy of the 1/100 solution was tested by adding 1 ml of a 1/10 solution of the original combined solutions to 9 ml of oocyst suspension.

The diluted solutions containing occysts were then held at 4° C. or 20° C. and samples were taken after 1 hour, 6 hours and 24 hours to see whether the oocysts had been killed.

After incubation the diluted solutions containing the oocyst suspensions were centrifuged. Following centrifugion the oocysts were washed several times in PBS. The oocysts were then re-suspended in 1.4% solution of sodium bicarbonate to which phenol red had been added. Carbon dioxide gas was bubbled through until the indicator colour was lost giving a pH of 6.8. After overnight incubation at 37° C. the oocysts were again centrifuged and washed with PBS. They were finally resuspended in PBS. Glass balls were added and the suspension shaken thoroughly. An aliquot of fluid was removed and added to a drop of excysting fluid (0.25% trypsin, with 0.5% bile in PBS). This suspension was incubated at 37° C. for up to 75 minutes or until excystment was seen to occur.

Excystment was deemed not to have occurred if less than 1% of the oocysts excysted. A control suspension of oocysts was handled in parallel with the other procedures to ensure that the oocyst suspensions were viable. The results were as follows ("+"=excystment):

|  | Exposure time | | | |
| --- | --- | --- | --- | --- |
|  | 1 h | 6 h | 24 h | Control |
| Eimeria tenella at +4° C. Dilution | | | | |
| 1/1 | − | − | − | |
| 1/10 | − | − | − | + |
| 1/100 | + | + | − | |
| at +20° C. | | | | |
| 1/1 | − | − | − | |
| 1/10 | − | − | − | + |
| 1/100 | + | − | − | |
| Eimeria necatrix at +4° C. Dilution | | | | |
| 1/1 | − | − | − | |
| 1/10 | + | + | − | + |
| 1/100 | + | + | + | |
| at +20° C. | | | | |
| 1/1 | − | − | − | |
| 1/10 | + | + | − | + |
| 1/100 | + | + | + | |
| Eimeria brunetti at +4° C. Dilution | | | | |
| 1/1 | − | − | − | |
| 1/10 | + | + | − | + |
| 1/100 | + | + | + | |
| at +20° C. | | | | |
| 1/1 | − | − | − | |
| 1/10 | + | + | − | + |
| 1/100 | + | + | + | |
| Eimeria acervulina at +4° C. Dilution | | | | |
| 1/1 | + | − | − | |
| 1/10 | + | + | − | + |
| 1/100 | + | + | + | |
| at +20° C. | | | | |
| 1/1 | + | − | − | |
| 1/10 | + | + | − | + |
| 1/100 | + | + | + | |

These results show that the materials of the invention were most effective against Eimeria tenella. Eimeria tenella, Eimeria necatrix and Eimeria brunetti could all be inactivated within 1 hour of exposure of the materials.

Although Eimeria acervulina showed a greater degree of resistance to inactivation even this strain was inactived after exposure of between 1 and 6 hours.

There was no significant temperature related effect. The two temperatures were chosen as representative of winter and summer ambient temperatures. Thus the same effects will be found both summer and winter.

I claim:

1. A method of disinfecting a surface from oocysts, which method comprises the steps of:
   (a) combining together an ammonium salt, a surfactant and an indicator having a colour change in the range pH 8 to pH 10 in a first aqueous solution;
   (b) combining together an alkali metal hydroxide and a bactericide in a second aqueous solution;
   (c) applying said first aqueous solution of a surface so as to effect thorough wetting of said surface;
   (d) thereafter applying enough of said second aqueous solution to said surface so that said indicator changes colour indicating the in situ generation of ammonia on said surface; and
   (e) permitting said ammonia to remain in contact with said surface for a time period sufficient to disinfect said surface from oocysts.

2. A method according to claim 1, wherein said first aqueous solution comprises a 0.5 to 1.5 molar solution of said ammonium salt, and said second aqueous solution comprises a 0.75 to 2.3 molar solution of said alkali metal hydroxide, and the molar concentration of said hydroxide is greater than the molar concentration of said ammonium salt.

3. A method according to claim 2, wherein the concentration of the ammonium salt in the first aqueous solution is 0.8 to 1.0 molar and the concentration of hydroxide in the second aqueous solution is 1.2 to 1.5 molar

* * * * *